US008034963B2

(12) United States Patent
Ng

(10) Patent No.: US 8,034,963 B2
(45) Date of Patent: Oct. 11, 2011

(54) PROCESS FOR REFINING FATS AND OILS

(75) Inventor: Daniel Ng, Kuala Lumpur (MY)

(73) Assignee: Alfa Laval Corporate AB, Lund (SE)

( * ) Notice: Subject to any disclaimer, the term of this patent is extended or adjusted under 35 U.S.C. 154(b) by 584 days.

(21) Appl. No.: 12/279,205

(22) PCT Filed: Feb. 9, 2007

(86) PCT No.: PCT/SE2007/000120

§ 371 (c)(1),
(2), (4) Date: Oct. 29, 2008

(87) PCT Pub. No.: WO2007/094713

PCT Pub. Date: Aug. 23, 2007

(65) Prior Publication Data

US 2009/0050536 A1 Feb. 26, 2009

(30) Foreign Application Priority Data

Feb. 15, 2006 (SE) ...................................... 0600339

(51) Int. Cl.

| | |
|---|---|
| ***C07C 51/42*** | (2006.01) |
| ***C11B 3/04*** | (2006.01) |
| ***C11B 3/10*** | (2006.01) |
| ***C10G 25/00*** | (2006.01) |
| ***C10G 17/00*** | (2006.01) |
| ***B01D 19/00*** | (2006.01) |

(52) U.S. Cl. .............. 554/175; 96/181; 96/201; 196/46; 196/46.1; 208/256; 208/302; 426/488; 554/190; 554/191; 554/204

(58) Field of Classification Search ........................ None
See application file for complete search history.

(56) References Cited

U.S. PATENT DOCUMENTS 4,089,880 A * 5/1978 Sullivan ........................ 554/191
4,230,630 A * 10/1980 Mag et al. ..................... 554/191

FOREIGN PATENT DOCUMENTS

EP 0580896 10/1992
EP 1258524 11/2002

* cited by examiner

*Primary Examiner* — Glenn Caldarola
*Assistant Examiner* — Randy Boyer
(74) *Attorney, Agent, or Firm* — Michaud-Kinney Group LLP

(57) ABSTRACT

The present invention relates to a process for cooling fatty acid distillate from scrubbing section in a fats and oils refinery comprising cooling the fatty acid distillate by heat recovery in at least one heat-exchanging zone with refined oils having a temperature above about 50° C. heating the refined fats and oils to a temperature above about 70° C. The present invention relates further to a process for refining crude fats and oils, and refining plant for refining crude fats and oils.

16 Claims, 3 Drawing Sheets

PROCESS FOR REFINING FATS AND OILS

The present invention relates to a process for cooling fatty acid distillates (FAD) from deacidification and deodorisation section in a fats and oils refinery, a process for refining fats and oils, and a refining plant.

BACKGROUND

Conventional refining processes for refining fats and oils are using clean cooling water to cool both fatty acid distillates and the hot deodorised oils in heat exchangers. Since water and especially clean water is a resource, which in many parts of the world is very limited and often poor quality, therefore, there is a need for alternative cooling systems or cooling fluids, or to eliminate the use of clean cooling water.

Examples of processes for refining oils are disclosed by WO95/33809, WO86/04603, U.S. Pat. No. 4,089,880, U.S. Pat. No. 3,999,966, GB704232 and GB704232.

An aim for the present invention is to find an alternative process for the cooling of fatty acid distillates.

Another aim is to improve the heat recovery balance for production of refined oils.

Yet another aim is to improve the continuous process of crude oils and thus achieving high heat recovery and lower operating costs.

SUMMARY

Accordingly the present invention provides a new process concept, which eliminates the requirement of clean water as a cooling medium when producing refined oils in refinery processes of fats and oils, which are hereinafter referred to as oils. The new concept requires very high heat recovery in refining processes, and is providing outgoing refined oils having low temperature. The hot refined oils or deodorised oils may be heat exchange in heat-exchanging zones with bleached oils from bleaching section and/or incoming crude oils. The cooled refined oils may then be used for cooling hot fatty acid distillate in at least one heat-exchanging zone according to one alternative of the invention. The use of heat recovery of heating cool refined oils and of cooling hot fatty acid distillates may thus eliminate the use of cooling water.

The new process concept relates to a process for cooling fatty acid distillate from deacidification/deodorization section in oils refinery comprising cooling the fatty acid distillate by heat recovery in at least one heat-exchanging zone with refined oils having a temperature above about 40° C., heating the refined oils to a temperature above about 60° C. According to one alternative of the process may the above about 60° C. refined oils being loaded to a dry fractionation or winterisation section. In the dry fractionation or winterisation section may liquid oils be control chilled to form partial solid fats before separating by use of separation equipments. According to another alternative process may the fatty acid distillate being cooled from a temperature above about 80° C. to a temperature below about 60° C. According to yet another alternative process may the fatty acid distillate having a temperature within a range from about 85° C. to about 65° C. being cooled to a temperature within a range from about 65° C. to about 50° C. According to a further alternative process may the fatty acid distillate having a temperature within a range from about 80° C. to about 70° C. being cooled to a temperature within a range from about 65° C. to about 55° C. According to a further alternative process may refined oils having a temperature within a range from about 45° C. to about 55° C., and the refined oils being heated to a temperature above about 70° C., and loading the above about 70° C. refined oils to a dry fractionation or winterisation section. According to a further alternative process may the at least one heat-exchanging zone being single or multiple units of heat exchangers arranged in parallel or in series. According to a further alternative process may the single or multiple units of heat exchangers being selected from a group consisting of gasketed plate heat exchangers, shell and tube heat exchangers, welded plate heat exchangers, brazed plate heat exchangers, spiral heat exchanger, heat recovery stainless steel coils within a section to be temperated, or combinations thereof.

The new process concept relates also to a process in which crude oils is heated to a bleaching temperature below about 140° C. in a heat recovery operation, according to one alternative process may the crude oils be heated to a bleaching temperature below about 120° C., or according to another alternative process may the bleaching temperature below about 105° C. In the heat recovery operation, refined oils being cooled by to above or at about 60° C., according to one alternative process may the refined oils be cooled to above or at about 50° C., according to another alternative process may the refined oils be cooled to above or at above 40° C. The heated crude oils are mixed with phosphoric acid or citric acid to treat the phosphatides or gums, and other impuritic materials. The treated phosphatides and other impuritic materials are removed in a subsequent bleaching and filtration section, and are mixed with adsorbents in the bleaching and filtration section under vacuum. The pigments and other oxidizing materials are adsorbed by the adsorbents. According to one alternative process may the adsorbents be bleaching earth, silica gel, activated carbon, etc or combinations thereof. The adsorbents, and the adsorbed pigments and other oxidizing materials are filtered off from the treated oils. This treated and filtered oils are called the bleached oils. The bleached oils may require further treatment in the deacidification/deodorisation section. The bleached oils are then deaerated and heated by heat recovery in a heat-exchanging zone with hot deodorised oils. Finally may the bleached oils be heated with a heating medium in a deacidification/deodorisation section according to one alternative embodiment of the invention to deodorisation temperature below 300° C. According to one alternative may the bleached oils be heated to a temperature from about 200° C. to about 280° C. According to one alternative process may the bleached oils be finally heated with a heating medium to deodorisation temperature from about 230° C. to about 280° C. According to another alternative process may the bleached oils be finally heated with a heating medium to deodorisation temperature from about 240° C. to about 270° C. The heating medium may be high-pressure steam, but any other suitable heating medium may be used for examples thermal oil heating, direct electric heating, etc.

Deodorising of the oils by distilling off volatile compounds such as for instance free fatty acids and various odoriferous compounds in a joint action zone by use of vacuum, high temperature and stripping steam. The deodorisation section has sufficient holding time for heat bleaching. During the holding, some heat sensitive compounds in the oil are decomposed by thermal action resulting in colour reduction.

After deodorising, the hot deodorised oil is discharge by a pump. After pre-cooling the deodorised oils by incoming bleached oils in heat-exchanging zone, anti-oxidant such as for example but not limited to diluted citric acid is injected and the oils are dried to reduce the moisture content. The deodorised oils are further cooled by heat recovery in a crude oil heat-exchanging zone at the gum pre-treatment/bleaching section to a temperature above or at approximately 60° C., according to one alternative process may the refined oils be cooled to above or at approximately 50° C., according to another alternative process may the refined oils be cooled above or at approximately 40° C. The cooled oils are sent to the storage as refined oils sometimes refers to as refined, bleached and deodorised oils. According to another alternative process may the refined oils be cooled to a temperature within a range from about 45° C. to about 55° C.

According to one alternative embodiment may the cooled refined oils be loaded directly to a dry fractionation section, the cooled refined oils may be used to heat exchange with the fatty acid distillate in a heat-exchanging zone. While the hot fatty acid distillate are cooled, the cool refined oils are warmed up again to above 65° C., according to one alternative up to above 70° C., according to another alternative up to above 75° C. This temperature of the refined oils is sufficient to melt solid fats. The oils enter the dry fractionation or winterisation section without any further steam heating. Such arrangement will eliminate the traditional requirement of cooling water to cool both the refined oils and the fatty acid distillates in two heat exchanger zones, and such arrangement will also reduce the steam heating requirement in the dry fraction or winterisations section, thus another energy saving.

To recover fatty acids and other condensable components, vapor from the deodoriser is recovered in a scrubber section. The vapor is condensed by contact with circulated cooled fatty acid distillate. According to one alternative may the temperature of the vapor be over about 180° C. before condensing by contact with circulated cool fatty acid distillate. According to another alternative may the temperature of the vapor be over about 200° C. before condensing by contact with circulated cool fatty acid distillate. According to another alternative may the temperature of the vapor be over about 220° C. before condensing by contact with circulated cool fatty acid distillate. The circulated cooled fatty acid distillates are heated, the condensed vapor and the recovered fatty acid distillates are accumulated in the bottom of the scrubber, or stored in a tank and/or intermittently sent to storage as by-products. The temperature of the recycled fatty acid distillate is maintained by heat exchange with the refined oil in the heat recovery zone at a temperature within a range from about 40° C. to about 70° C. According to one alternative process is the temperature of the recycled fatty acid distillate is maintained by heat exchange with the refined oil in the heat recovery zone at a temperature within a range from about 45° C. to about 65° C. According to another alternative process is the temperature of the recycled fatty acid distillate is maintained by heat recovery with the refined oil in the heat recovery zone at a temperature of about 60° C. Cooling fatty acid distillate by heat exchange with out-going refined oils in the oil refinery processes thus saves both cooling water and energy.

According to a further alternative process may the at least one heat-exchanging zone being single or multiple units of heat exchangers arranged in parallel or in series. According to a further alternative process may the single or multiple units of heat exchangers being selected from a group consisting of gasketed plate heat exchangers, shell and tube heat exchangers, welded plate heat exchangers, brazed plate heat exchangers, spiral heat exchanger, heat recovery stainless steel coils within a section to be temperated, or combinations thereof.

Suitable gasketed plate heat exchanger according to the invention may be comprised of a pack of corrugated metal plates with portholes for the passage of two fluids between which heat transfer will take place. The plate pack may be assembled between a frame plate and a pressure plate and be compressed by tightening bolts. The plates may be fitted with a gasket, which seals the channel and is directing the fluids into alternate channels. The number and size of the plates are determined by the flow rate, physical properties of the fluids, pressure drop and temperature program. The corrugations of the plates may promote fluid turbulence and may support the plates against differential pressures.

Suitable welded plate heat exchanger according to the invention may be comprised of a pack of corrugated metal plates with portholes for the passage of two fluids between which heat transfer will take place. The plate pack may be assembled between a frame plate and a pressure plate and be compressed by tightening bolts. The plates may be welded, which seals the channels and directs the fluids into alternate channels. The number and size of the plates are determined by the flow rate, physical properties of the fluids, pressure drop and temperature program. The plate corrugations may promote fluid turbulence and may support the plates against differential pressures.

Suitable brazed plate heat exchanger according to the invention may be comprised of a pack of corrugated metal plates with portholes for the passage of two fluids between which heat transfer will take place. The plate pack may be assembled between a frame plate and a pressure plate and compressed by tightening bolts, but there a brazed heat exchanger may be without a frame. The plates may be brazed which seals the channels and directs the fluids into alternate channels. The number and size of the plates are determined by the flow rate, physical properties of the fluids, pressure drop and temperature program. The plate corrugations promote fluid turbulence and support the plate against differential pressure.

Examples of suitable heat exchangers according to the invention are, but not limited to, those which are disclosed by WO 93/15369, WO 95/31681, WO 95/31682, and WO 96/09513.

Examples of fatty acid distillates according to the invention are, but not limited to palm fatty acid distillate, palm kernel fatty acid distillate, coconut oil fatty acid distillate, tallow or lard fatty acid distillates, fatty acid distillates from various seed oils, fatty acid distillates from various exotic fats and oils, etc.

Fatty acid distillates in this invention are classified as, but not limited to mixture of free fatty acids, triglycerides, diglygerides, monoglycerides, glycerol, sterols, tocopherols, tocotrienols, odoriferous matters such as aldehydes and ketones and all other volatile matters.

Fats and oils in this invention are classified as, but not limited to palm oil, palm kernel oil, coconut oil, tallow, lard, soybean oil, canola or rapeseed oil, cottonseed oil, corn or maize oil, sunflower oil, safflower oil, rice bran oil, olive oil, cocoa butter, sal fats, illipe butter, shea butter, milk butter, fish oils, groundnut oil, various types of exotic fats and oils, oil-derivatives such as ethyl or methyl esters, etc.

In generally accepted terms, fats are classified as solid at room temperature and oils are classified as liquid at room temperature. Fats will melt upon heating above their melting point.

The present invention relates also to a refining plant for refining crude oils, which plant comprises at least two heat-exchanging zones for recovery of heat from hot refined oils, at least one bleaching and filtration section, and at least one deodorization section, wherein the heat-exchanging zones being single or multiple units of heat exchangers arranged in parallel or in series, and the heat exchangers being selected from a group consisting of gasketed plate heat exchangers, shell and tube heat exchangers, welded plate heat exchangers, brazed plate heat exchangers, spiral heat exchanger, heat recovery stainless steel coils within a section to be temperated, or combinations thereof.

The present invention relates also to a refining plant for refining crude oils which system comprises at least two heat-exchanging zones for recovery of heat from hot refined oils, at least one bleaching and filtration section, and at least one deodorization section. The heat-exchanging zones being single or multiple units of heat exchangers arranged in parallel or in series. At least one of the heat exchangers being a vacuum vessel, which comprises spaces through which the oils to be treated is brought to pass, means to heat or cool the oil in form of U-tubes. Perforated pipes arranged at the bottom of said spaces are arranged to lead stripping gas into said oil. The vessel has a connection to a vacuum source, and the spaces in the vessel are arranged such that the oil passes through the vessel by gravity. A heating or cooling medium is passing said means, and the medium is arranged to be pumped there through. The U-tubes for heating or cooling medium are arranged in such a way in said spaces that the flow of oil is counter-current to the flow of heating or cooling medium all through the vessel and that a number of U-tubes are arranged in groups, parallel and in rows above each other in said spaces. Examples of suitable vacuum vessels which may be used, but not limited to, according to the invention are disclosed in WO 95/33809 or in SE 0501008-7.

In the following, the invention will be explained by the use of FIGS. 1 to 3. The figures are for the purpose of demonstrating the invention and are not intended to limit its scope.

DETAILED DESCRIPTION

Figure 1:
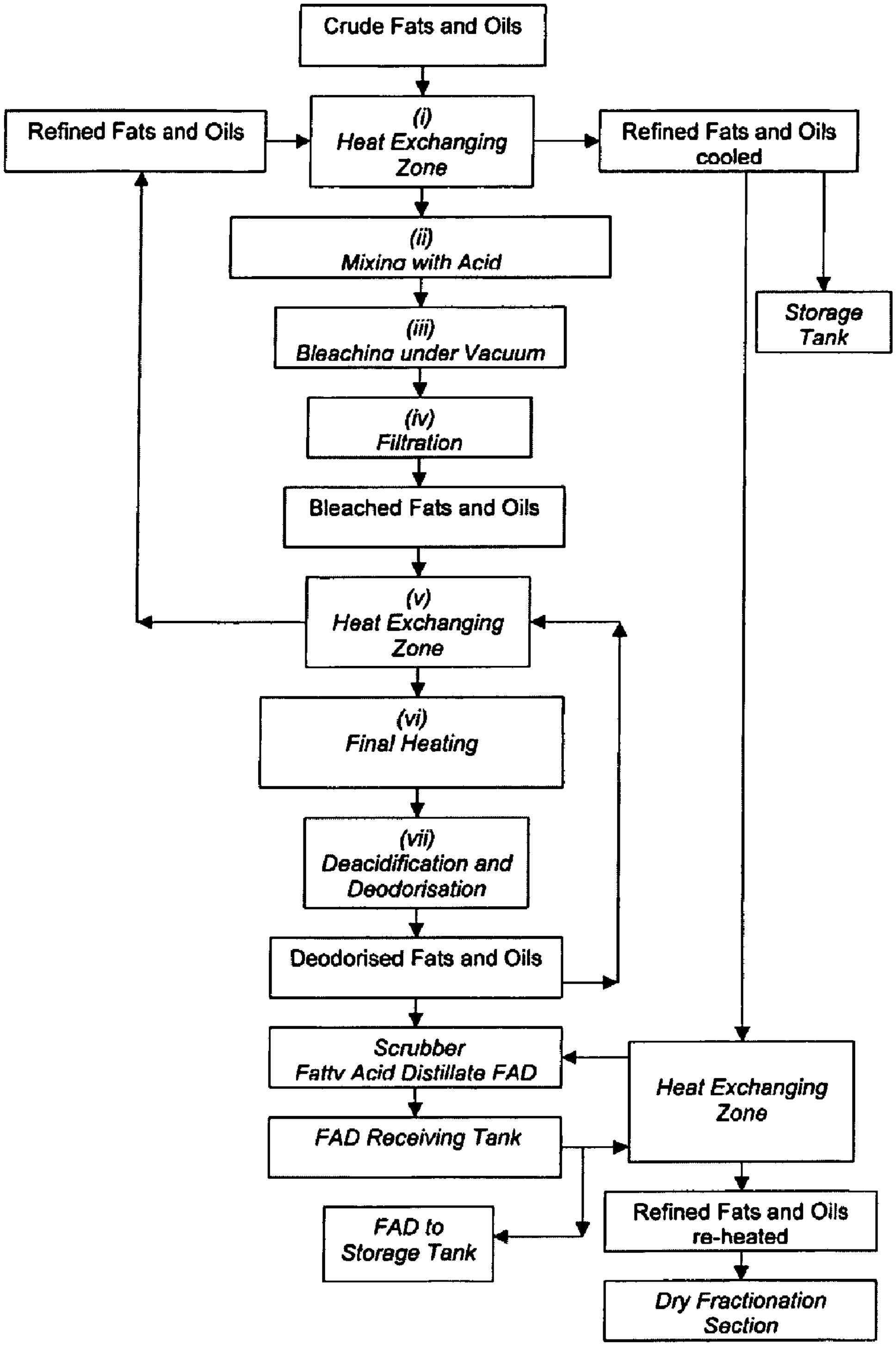
FIG. 1 shows a flow-chart of a fats and oils refinery process according to one alternative embodiment of the invention.

FIG. 1 shows a schematic oils refinery process according to one embodiment in a flow-chart form and shows the steps of:

(i) Heating cold crude oils to a bleaching temperature and at the same time cooling hot refined or deodorised oils, hereinafter called refined oils, from step (v) by heat recovery in a heat-exchanging zone, and pumping the cooled refined oils to storage or reheating the cooled refined oils by heat recovery in a heat-exchanging zone with hot fatty acid distillates from scrubbing section. According to one alternative embodiment of the present invention may the crude oils have a temperature below about 40° C., and the crude oils are heated to a bleaching temperature below about 140° C. According to another alternative are the crude oils heated to a bleaching temperature below about 130° C. According to yet another alternative are the crude oils heated to a bleaching temperature below about 120° C. According to yet another alternative are the crude oils heated to a bleaching temperature below about 110° C. The hot refined oils from step (v) may have a temperature above about 100° C. according to one alternative of the invention. According to another alternative may the refined oils from step (v) have a temperature above about 110° C. According to yet another alternative may the refined oils from step (v) have a temperature above about 120° C. The hot refined oils from step (v) may be cooled to a temperature above about 40° C. according to one alternative of the invention. According to another alternative may the refined oils be cooled to a temperature above 50° C. The cooled refined oils by heat recovery in a heat-exchanging zone to a temperature above about 70° C. with hot fatty acid distillates from scrubbing section.

(ii) Mixing the heated crude oils with phosphoric acid or citric acid or combinations thereof to treat phosphatides or gums, and impure materials;

(iii) Adsorbing the treated phosphatides or gums, and impure materials by the adsorbents in the bleaching section under vacuum.

(iv) Removing by filtration the adsorbents and adsorbed materials in the filtration section.

(v) Deaerating and heating the bleached oils from step (iv) by heat recovery in a heat-exchanging zone with the hot refined oils from step (vi) and cooling the hot refined oils from step (vi) in the heat-exchanging zone. According to one alternative of the invention are the refined oils cooled to a temperature above about 100° C. According to another alternative of the invention are the refined oils cooled to a temperature above about 110° C. According to yet another alternative of the invention are the refined oils cooled to a temperature above about 120° C.

(vi) Heating and refining the oils from step (v) in a deacidification/deodorization section with a heating medium to a deacidification/deodorization temperature below about 300° C. and distilling off fatty acid distillate (FAD) and volatiles and odoriferous matters.

Figure 2:
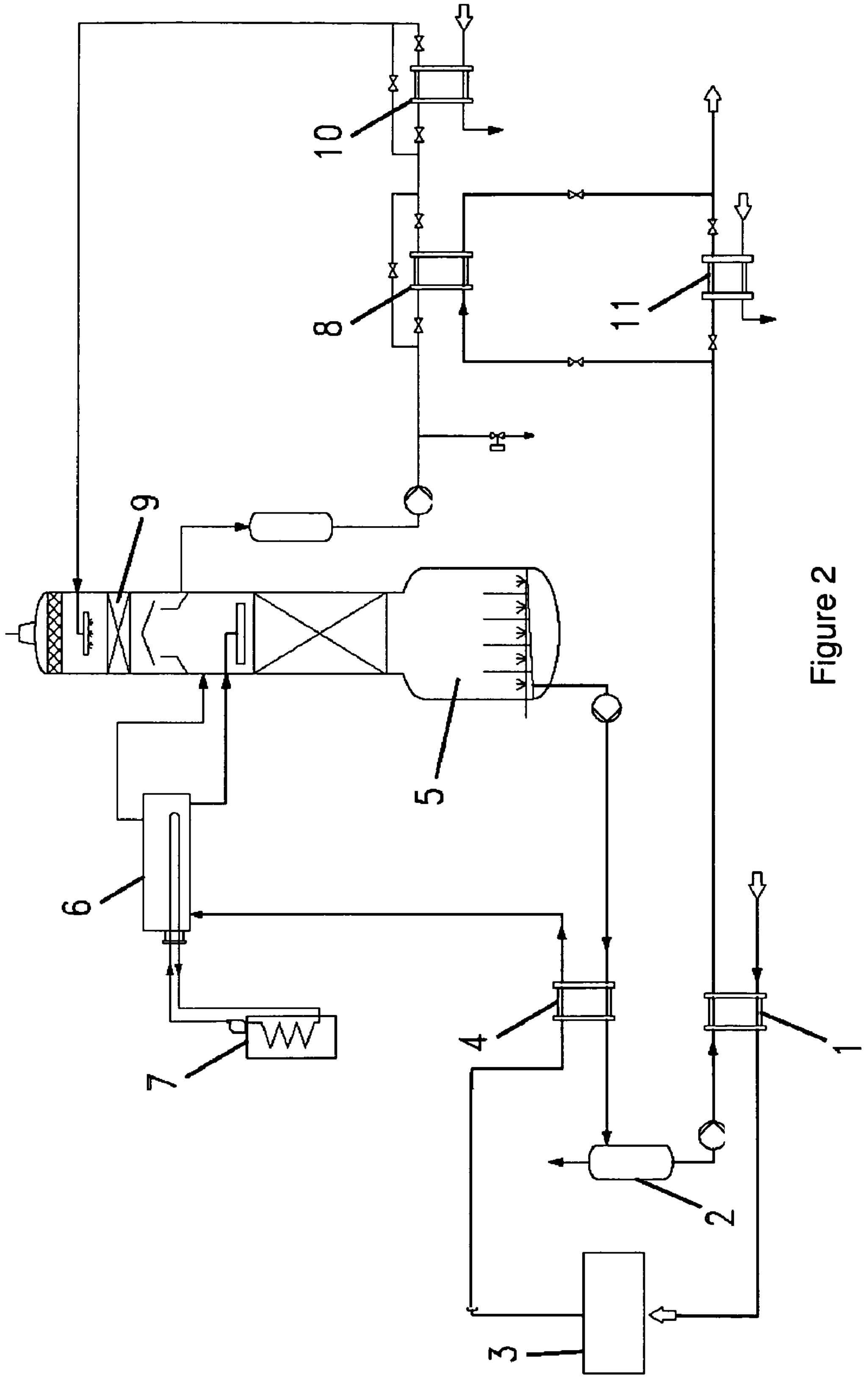
FIG. 2 shows a fats and oils refinery process according to another alternative embodiment of the invention.

FIG. 2 shows an alternative embodiment of the oils refinery process. Crude oils are heated in heat-exchanging zone 1 with hot deodorised oils coming from dryer 2 in which moisture is taken away. The heated crude oils are degummed and bleached in bleaching section 3 by mixing the oils with phosphoric acid or with citric acid, or combinations thereof, reacting and adsorbing the impurities under vacuum and removing them. Adsorbed pigments and other impurities are removed by filtration. Heating the bleached oils in heat-exchanging zone 4 with hot deodorised oils from deacidification/deodorisation section 5. Heating the bleached oils to deodorisation temperature in a heating section 6 with a heating medium 7 to a deodorisation temperature below about 300° C. According to one alternative of the invention may the bleached oil be heated to a deodorisation temperature within a range of from about 200° C. to about 280° C. The final oil temperature for the oils varies for different types of oils. According to one alternative are the cooled refined oils from heat-exchanging zone 1 reheated in heat-exchanging zone 8 to above about 70° C. with hot fatty acid distillate from scrubber section 9. The fatty acid distillate may be recycled or stored as by products. The temperature of the recycled fatty acid distillate may be maintained by heat exchange with the refined oil in heat recovery zone 8 at a temperature within a range from about 40° C. to about 70° C.

Fatty acid distillate cooler zone 10 and refined oil cooler zone 11 are used during start-up or shut-down operation only. In normal operation, these clean water coolers are stopped and bypassed.

Figure 3:
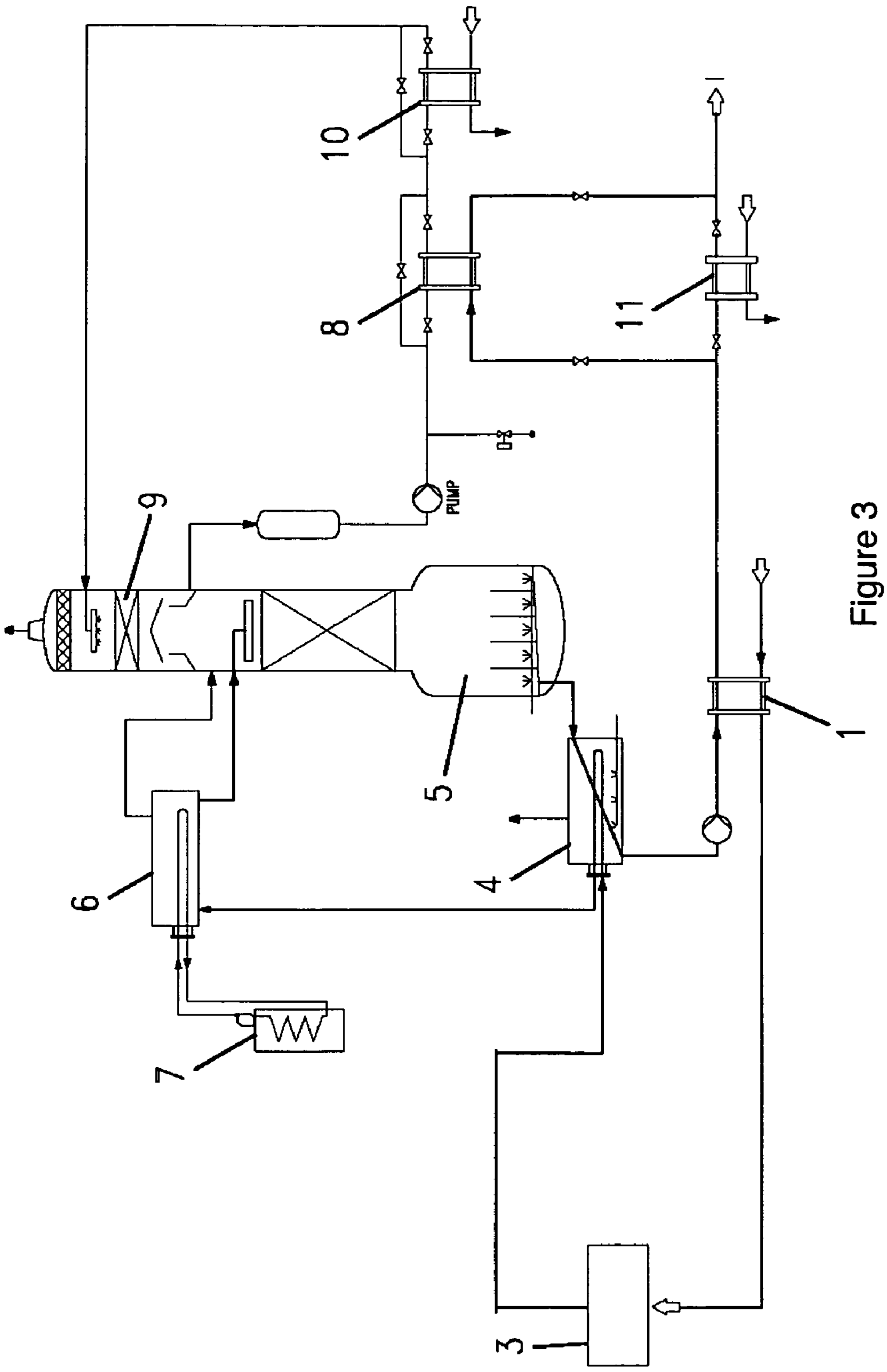
FIG. 3 shows a fats and oils refinery process according to yet another alternative embodiment of the invention.

FIG. 3 shows another alternative embodiment of the oils refinery process. According to this embodiment are the bleached oils from bleaching section 3 heated with hot refined oils from deodorization section 5 in a heat exchanger zone 4. Heat exchanger zone 4 according to this embodiment is a vacuum vessel. The vacuum vessel comprises details which are not shown in FIG. 3 and includes spaces through which the oils to be treated is brought to pass, means to heat or cool the oil in form of U-tubes. Perforated pipes arranged at the bottom of said spaces are arranged to lead stripping gas into said oil. The vessel has a connection to a vacuum source, and the spaces in the vessel are arranged such that the oil passes through the vessel by gravity. A heating or cooling medium is passing said means, and the medium being arranged to be pumped there through. The U-tubes for heating or cooling medium are arranged in such a way in said spaces that the flow of oil is counter-current to the flow of heating or cooling medium all through the vessel and that a number of U-tubes are arranged in groups, parallel and in rows above each other in said spaces.

What is claimed is:

1. A process for refining crude fats and oils, which process comprises:

(i) heating cold crude fats and oils to a bleaching temperature and cooling hot refined oils from step (v) by heat recovery in a heat-exchanging zone, and pumping the cooled refined oils to storage or reheating the cooled refined oils by heat recovery in a heat-exchanging zone with hot fatty acid distillates from scrubbing section;

(ii) mixing the heated crude fats and oils with phosphoric acid, citric acid or mixtures thereof to treat phosphatides, gums and impure materials;

(iii) adsorbing the treated phosphatides, gums and impure materials by the adsorbents in the bleaching section under vacuum;

(iv) removing by filtration the adsorbents and adsorbed materials in the filtration section;

(v) deaerating and heating the bleached fats and oils from step (iv) by heat recovery in a heat-exchanging zone with the hot refined oils from step (vi) and cooling the hot refined oils from step (vi) in the heat-exchanging zone; and (vi) heating and refining the oils from step (v) in a deacidification/deodorization section with a heating medium to a deacidification/deodorization temperature and distilling off fatty acid distillates, volatiles, and odoriferous matters.

2. The process according to claim 1, wherein step (i) the refined oils being cooled to a temperature above about 40° C.

3. The process according to claim 2, wherein step (i) the refined oils being cooled to a temperature above about 50° C.

4. The process according to claim 1, wherein step (i) crude fats and oils are heated to a bleaching temperature below about 120° C.

5. The process according to claim 4, wherein step (i) crude fats and oils are heated to a bleaching temperature below about 110° C.

6. The process according to claim 1, wherein in step (vi) the deodorisation temperature being within a range of from about 200° C. to about 280° C.

7. The process according to claim 1, wherein the heat-exchanging zones are single or multiple units of heat exchangers arranged in parallel or in series.

8. The process according to claim 7, wherein the heat-exchanging zones are single or multiple units of heat exchangers selected from a group consisting of gasketed plate heat exchangers, shell and tube heat exchangers, welded plate heat exchangers, brazed plate heat exchangers, spiral heat exchanger, heat recovery stainless steel coils within a section to be temperated, or combinations thereof.

9. The process according to claim 1, wherein fatty acid distillate (FAD) from a scrubbing section in a fats and oils refinery are cooled by heat recovery in at least one heat-exchanging zone with refined oils having a temperature above about 40° C., heating the refined oils to a temperature above about 60° C.

10. The process according to claim 9, wherein the refined oils have a temperature above about 60° C. being loaded to a dry fractionation or winterisation section.

11. The process according to claim 9, wherein the fatty acid distillate is cooled from a temperature above about 80° C. to a temperature below about 60° C.

12. The process according to claim 9, wherein the fatty acid distillate has a temperature within a range from about 85° C. to about 65° C. and is cooled to a temperature within a range from about 65° C. to about 50° C.

13. The process according to claim 9, wherein the fatty acid distillate has a temperature within a range from about 80° C. to about 70° C. and is cooled to a temperature within a range from about 65° C. to about 55° C.

14. The process according to claim 9, wherein refined oils have a temperature within a range from about 45° C. to about 55° C., and the refined oils are heated to a temperature above about 70° C., and loading the above about 70° C. refined oils to a dry fractionation or winterisation section.

15. A refining plant for refining crude fats and oils to accomplish the process according to claim 1 comprising at least two heat-exchanging zones for recovery of heat from hot refined oils, at least one bleaching and filtration section, and at least one deodorisation section, wherein the heat-exchanging zones being single or multiple units of heat exchangers arranged in parallel or in series, and the heat exchangers being selected from a group consisting of gasketed plate heat exchangers, shell and tube heat exchangers, welded plate heat exchangers, brazed plate heat exchangers, spiral heat exchanger, heat recovery stainless steel coils within a section to be temperated, or combinations thereof.

16. A refining plant for refining crude fats and oils to accomplish the process according to claim 1 comprising at least two heat-exchanging zones for recovery of heat from hot refined oils, at least one bleaching and filtration section, and at least one deodorization section, wherein the heat-exchanging zones being single or multiple units of heat exchangers arranged in parallel or in series, wherein at least one of the heat exchangers being a vacuum vessel for which vessel comprises spaces through which the oil to be treated is brought to pass, means to heat or cool the oil in form of U-tubes, perforated pipes arranged at the bottom of said spaces to lead stripping gas into said oil, which vessel has a connection to a vacuum source and which spaces in the vessel are arranged such that the oil passes through the vessel by gravity and a heating or cooling medium passing said means is arranged to be pumped there through, and wherein the U-tubes for heating or cooling medium are arranged in such a way in said spaces that the flow of oil is counter-current to the flow of heating or cooling medium all through the vessel and that a number of U-tubes are arranged in groups, parallel and in rows above each other in said spaces.

* * * * *